(12) United States Patent
Sanna

(10) Patent No.: US 8,366,648 B2
(45) Date of Patent: Feb. 5, 2013

(54) MEDICAL CONNECTOR ABLE TO CONNECT SPECIFIC MEDICAL TUBE AND INPUT PORT

(75) Inventor: Salvatore Sanna, Mirandola (IT)

(73) Assignee: Gambro Lundia AB, Lund (SE)

( * ) Notice: Subject to any disclaimer, the term of this patent is extended or adjusted under 35 U.S.C. 154(b) by 499 days.

(21) Appl. No.: 12/742,629

(22) PCT Filed: Nov. 4, 2008

(86) PCT No.: PCT/IB2008/002952
§ 371 (c)(1),
(2), (4) Date: May 12, 2010

(87) PCT Pub. No.: WO2009/063281

PCT Pub. Date: May 22, 2009

(65) Prior Publication Data
US 2010/0243543 A1    Sep. 30, 2010

(30) Foreign Application Priority Data
Nov. 16, 2007    (IT) .............................. MO2007A0342

(51) Int. Cl.
*A61M 37/00*    (2006.01)
(52) U.S. Cl. ..................... 604/5.04; 604/4.01; 604/5.01; 604/6.09; 604/533
(58) Field of Classification Search .................. 604/4.01, 604/5.01, 5.04, 6.09, 533; 285/317
See application file for complete search history.

(56) References Cited

U.S. PATENT DOCUMENTS

| | | | |
|---|---|---|---|
| 4,294,250 A | | 10/1981 | Dennehey |
| 4,439,193 A | | 3/1984 | Larkin |
| 4,541,457 A | * | 9/1985 | Blenkush ................. 137/614.06 |
| 5,033,777 A | | 7/1991 | Blenkush |
| 5,409,612 A | | 4/1995 | Maltais et al. |
| 5,591,143 A | | 1/1997 | Trombley, III et al. |
| 5,845,943 A | | 12/1998 | Ramacier, Jr. et al. |
| 5,890,517 A | * | 4/1999 | Laible ....................... 137/614.04 |
| 6,419,670 B1 | | 7/2002 | Dikeman |
| 6,676,652 B2 | | 1/2004 | Mogg |
| 7,070,589 B2 | | 7/2006 | Lolachi et al. |
| 2001/0042850 A1 | | 11/2001 | Cote et al. |
| 2002/0133136 A9 | | 9/2002 | Lolachi et al. |
| 2003/0184090 A1 | | 10/2003 | Guala |

(Continued)

FOREIGN PATENT DOCUMENTS

| | | |
|---|---|---|
| EP | 0 635 669 A1 | 1/1995 |
| EP | 0 856 332 A1 | 8/1998 |
| EP | 1 108 444 A2 | 6/2001 |
| EP | 1 181 946 A1 | 2/2002 |
| EP | 1 790 376 A1 | 5/2007 |
| WO | 2005/034833 A2 | 4/2005 |
| WO | 2005/068010 A2 | 7/2005 |

*Primary Examiner* — Leslile Deak
(74) *Attorney, Agent, or Firm* — Pearne & Gordon LLP

(57) ABSTRACT

A medical connector (18) has a visual signal (67) formed by a colored screen-applied band arranged on a bolt (63). In a correct engaged position of the bolt (63) with an external element, the signal is visible. In an incorrect engaged position, the part of the bolt (63) bearing the signal is lowered, so that the signal is hidden from view, providing an indication of a faulty situation. The medical connector serves to connect the end of a dialysate supply tube to an inlet port of a dialyser.

21 Claims, 15 Drawing Sheets

U.S. PATENT DOCUMENTS

| | | |
|---|---|---|
| 2004/0249349 A1 | 12/2004 | Wentling |
| 2005/0101939 A1 | 5/2005 | Mitchell |
| 2005/0197646 A1 | 9/2005 | Connell et al. |
| 2005/0234428 A1 | 10/2005 | Spohn et al. |
| 2006/0076772 A1 | 4/2006 | Zimmerman |
| 2006/0122559 A1 | 6/2006 | Shia et al. |
| 2006/0293628 A1 | 12/2006 | Hunt et al. |
| 2007/0075003 A1 | 4/2007 | Schmidt |

* cited by examiner

MEDICAL CONNECTOR ABLE TO CONNECT SPECIFIC MEDICAL TUBE AND INPUT PORT

BACKGROUND OF THE INVENTION

The invention relates to a medical connector, to an extracorporeal blood treatment apparatus comprising the medical connector, and to a dialysis machine provided with the medical connector. In particular the medical connector can be advantageously used for connecting a fluid transport line (for example a transport line of a fresh or used dialysis fluid) to a fluid access port (inlet or outlet) of a device for extracorporeal blood treatment of the semipermeable membrane type, such as for example a dialyser.

Specifically, though not exclusively, the present invention can be usefully applied for removably connecting the dialysate transport line of a dialysis monitor to a dialysate port of a semipermeable membrane dialyser or to a counter-connector connected to a fluid transport line arranged internally of a cabinet of a dialysis machine.

The prior art comprises various types of semipermeable membrane (dialysis filters) dialysers, which generally each define a blood chamber and a dialysate chamber which are separated from one another by a semipermeable membrane, for example of the hollow bundle type. Each dialyser is usually provided with two blood ports, one for blood inlet and the other for blood outlet, and two dialysate ports, one for the dialysate inlet and the other for the dialysate outlet. To begin the dialysis treatment, the two blood ports are connected to the arterial line and the venous line of an extracorporeal blood circuit, while the dialysate ports are connected to the supply line and the discharge line of the dialysate circuit controlled by the dialysis monitor. The dialysis monitor comprises actuators and sensors which control the correct progress of the dialysis treatment. The monitor for dialysis monitors that the fresh dialysate has the desired characteristics (in particular the temperature and the chemical composition) and that the patient's fluid balance respects a desired weight loss. Usually the supply line and the discharge line of the dialysate circuit each comprise a flexible tube which exits from a front panel of the dialysis monitor cabinet and which terminates with a connector configured for sealed removable coupling with the two dialysate ports of the dialyser. With the aim of readying the dialysis apparatus for the treatment, the operator must connect the dialysate circuit to the membrane dialyser: to this the operator manually takes the flexible tubes and couples the terminal connector with the dialysate port of the dialyser.

The dialysis machine is normally subjected to various procedures beyond the treatment itself, in which the dialysis fluid circuit is not connected to the membrane dialyser. These procedures can comprise, for example, washing and disinfection of the dialysis circuit, in which an operative fluid (chemical disinfectant, heated water, washing fluid, etc.) is placed in circulation along the dialysis fluid circuit. To enable complete circulation in all the circuit, the supply line and the discharge line of the dialysate circuit are connected in series to one another by a bypass block line arranged internally of the cabinet and provided at opposite ends thereof with two counter-connectors arranged on the front panel. The counter-connectors are coupled with the two connectors arranged at the ends of the two flexible tubes which form the end parts of the dialysate discharge.

A problem of dialysis machines of known type is the incorrect coupling of the terminal connectors of the dialysate circuit with the dialysate ports of the membrane dialyser or with the counter-connectors of the bypass block line. The incorrect coupling can lead to various drawbacks, in particular damage to parts of the dialysis apparatus, such as for example the detachment of tubes in the dialysate circuit or the breakage of elements (for example the pressure sensors of the dialysate circuit), or the loss of fluid in the incorrectly-coupled zone.

The prior art comprises various systems for verifying correct coupling of two parts of a medical fluid circuit.

Patent publication No. US 2007/0075003 describes a connector for connecting a dialysate port of a dialyser to a dialysate transport line, in which the blockage is realised by means of an undercut and an elastic element, such that it is audible.

U.S. Pat. No. 5,591,143 describes a luer-type connector provided with a coloured platelet which moves according to whether the connection has been made correctly or not.

U.S. Pat. No. 4,294,250 describes a luer connector provided with visual means for indicating that the connection has been made correctly.

Patent publication No. US 2002/0133136 describes a connector provided with visible means which enable determination of whether a positive blockage of the connection has been obtained or not.

Patent publication No. US 2003/0184090 illustrates a luer connector which reaches an engagement position with a click effect which produces a perceptible signal, in particular tactile and audible.

Patent publication No. WO 2005/068010 describes an adaptor provided with two tabs which enable a visual indication to be given of correct insertion of the adaptor internally of a catheter.

Patent No. EP 635669 illustrates a device for connecting a user to a source of medical gas, in which there are means for indicating a position of a connecting element in a connection box connected to the source. The indicator means can comprise two different colour surfaces which are visible through a window in two different positions, respectively parked and work positions, of the connecting element.

U.S. Pat. No. 6,676,652 describes an adapter for a catheter provided with a mobile arm forming an angle with the adapter body when the connecting mechanism is in the open position, while it is parallel to the adapter body when the catheter is engaged.

Patent publication no. EP 856332 describes an adapter for mounting a fluid transport device with a catheter tube, in which the bolt having an elliptic transversal section is rotatable with respect to the adapter body, also having an elliptic transversal section. The long axis and short axis of the bolt are aligned with the respective long and short axes of the adapter body in the locking position, and with the respective shot and long axes of the adapter body in the insertion position, thus providing a visual and tactile indication of the effective operative position of the bolt. Further, a lens provides an enlarged image of a recess which receives an end of the catheter in order to display the correct placing of the catheter.

Patent publication no. US 2006/0122559 describes a valve which can take on three positions. In an open position, an opening is aligned and in sealed fluid communication with an aspiration port. In an introduction position, the opening is aligned and in sealed fluid communication with an introduction port. In a closed position, there is no communication between the opening and the two above-mentioned ports. Visual evidence arranged on the external surface of the casing provide the indication of the effective position of the opening. The visual evidence can be a raised surface, a depression, a mechanical tooth, a light-emitting surface.

Patent publication no. US 2005/0197646 shows various embodiments of pairs of connectors for medical fluids, in which each pair of connectors is provided with feedback characteristics of audible, visual and tactile type which indicate that the coupling between the connectors has been completed.

SUMMARY OF THE INVENTION

An aim of the present invention is to provide a medical connector by virtue of which it is possible to reduce the risks which are consequent upon a faulty situation of incorrect connector coupling.

A further aim of the invention is to realise an extracorporeal blood treatment apparatus and a dialysis machine which are each provided with the medical connector.

An advantage of the invention is to realise a medical connector thanks to which is it possible easily to verify a faulty situation of incorrect connector coupling.

A further advantage of the invention is to provide a medical connector which is constructionally simple and economical.

A further advantage is to make a medical connector available which is simple and practical to use.

A still further advantage is to give rise to a medical connector thanks to which it is possible immediately and securely to verify any appearance of the faulty situation.

These aims and others besides are all attained by the present invention, as it is characterised by one or more of the appended claims.

Further characteristics and advantages and the present invention will better emerge from the detailed description of at least an embodiment of the invention, illustrated purely by way of non-limiting example in the accompanying figures of the drawings.

BRIEF DESCRIPTION OF THE DRAWINGS

The description will be made herein below with reference to the accompanying figures of the drawings, provided by way of non-limiting example.

DETAILED DESCRIPTION

Figure 1:
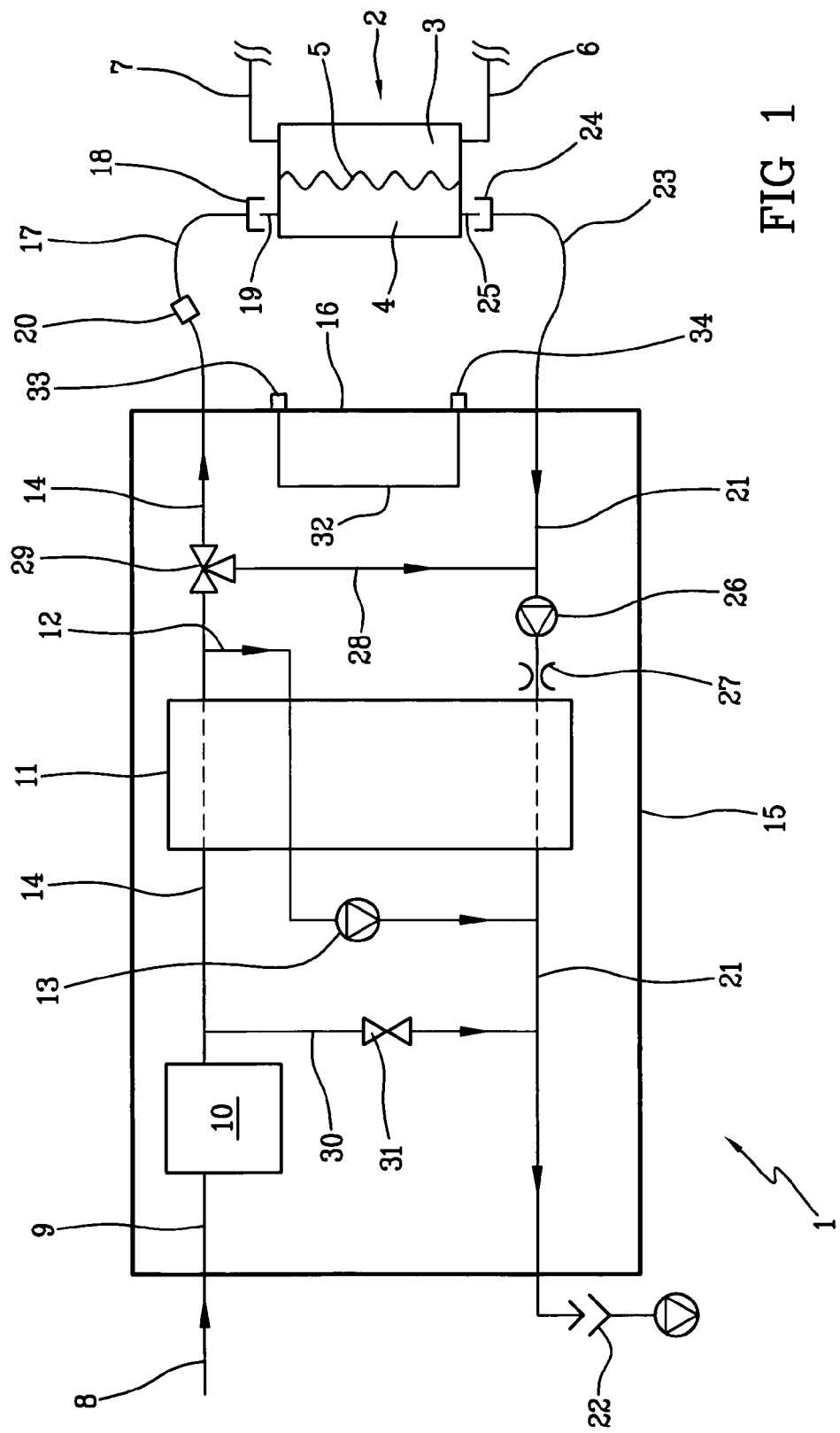
FIG. 1 illustrates a first version of an extracorporeal blood treatment apparatus, provided with a medical connector connected in accordance with the present invention.

With reference to FIG. 1, 1 denotes in its entirety an extracorporeal blood treatment apparatus. The apparatus can comprise an apparatus for dialysis, for hemo(dia)filtration, for ultrafiltration, for therapeutic plasma exchange, for hemoperfusion, for treatment of kidney failure, for treatment of congestive heart failure (CHF), and other types of treatment in which the extracorporeal blood comes into contact with a semipermeable membrane. In the specific case the apparatus in question comprises a dialysis machine.

The apparatus 1 comprises a blood treatment device 2 having a first chamber or blood chamber 3 and a second chamber or fluid chamber 4. The chambers 3 and 4 are separated from one another by a semipermeable membrane 5. The apparatus 1 comprises a blood circuit for connecting the blood chamber 3 with a patient. In the specific case the blood circuit comprises a blood removal line or an arterial line 6 and a blood return line or a venous line 7. The arterial line 6 is configured for removal of blood from a vascular access of a patient and for sending the blood to the blood chamber 3. The venous line 7 is configured for returning the treated blood from the blood chamber 3 to the vascular access of the patient. The blood circuit 6, 7 can comprise any one of the blood circuits or dialysis sets of known type used in a hemodialysis treatment or a hemo(dia)filtration treatment.

Optionally, the apparatus 1 (dialysis machine) comprises a fluid inlet 8 (water) and a transport line (9) which conducts the inlet fluid (water) from the fluid inlet 8 to a dialysate preparation device 10. The dialysate preparation device 10 can comprise any one of the devices of known type designed to prepare dialysate starting from water and concentrates. Optionally the dialysis machine comprises a fluid balance device for control of patient weight loss. The fluid balance device can comprise any one of known-type devices for patient fluid balance control (for example of the volumetric balance chamber type, of the double flow-meter type, of the differential flow-meter type, of the type of one or more gravimetric balances, etc.). In the specific case the fluid balance device comprises a volumetric system 11 (of known type and not described in detail) which ensures that the fluid volume entering the system equals the fluid volume that exits. The fluid balance device further comprises an ultrafiltration line 12 which bypasses the above-mentioned volumetric system 11 and which serves to regulate the patient weight loss. The ultrafiltration line 12 is provided with an ultrafiltration pump 13. A fresh dialysate supply line 14 connects the fresh dialysate source (the dialysate preparation device 10) with the fluid chamber 4 of the blood treatment device 2. Optionally the dialysis machine comprises a cabinet 15 which contains the dialysate preparation device 10 and the fluid balance device 11, 12. Optionally the fresh dialysate supply line 14 comprises a part of line which is internal of the cabinet, which terminates on a front panel 16 of the cabinet 15. Optionally, the fresh dialysate supply line 14 comprises a part of line 17 which is external of the cabinet 15 starting from the front panel 16 and terminating with a medical connector 18 configured for removable coupling with the access port 19 (fresh fluid inlet) to the fluid chamber 4 of the membrane blood treatment device 2. The part of line 17 external of the cabinet 15 comprises a flexible tube destined to be manually manoeuvred by an operator for connection and disconnection with the blood treatment device 2. Optionally the flexible tube can be provided with a removal port 20 to remove a sample of pre-dialysis fluid (of known type).

Optionally, the dialysis machine comprises a used dialysate discharge line 21 which connects the fluid chamber 4 of the blood treatment device 2 with a drainage 22 (of known type). The used dialysate discharge line 21 comprises a part of line internal of the cabinet 15 and a part of line 23 external of the cabinet 15. The part of line 23 which is external of the cabinet 15 has a first end connected to the front panel 16 of the cabinet and a second end provided with a medical connector 24 configured for removable connection with an access port 25 (outlet of used fluid) of the fluid chamber 4 of the blood treatment device 2. The part of line 23 which is external of the cabinet 15 compries a flexible tube which can easily be manoeuvred by an operator for connection to and disconnection from the blood treatment device 2. Optionally, the used dialysate discharge line 21 comprises a discharge pump 26, which can be controlled by the apparatus control unit. Optionally, the discharge line 21 can comprise a blood detector 27, for example an optic sensor which measured hemoglobin. Optionally, the discharge line 21 is connected to the supply line 14 by means of the ultrafiltration line 12. Optionally, a bypass line 28 is provided with connects the supply line 14 and the discharge line 21 and which is arranged between the fluid balance device 11, 12 and the blood treatment device 2. The bypass line 28 can be provided with a bypass valve 29. Optionally a further bypass line 30 (which can be provided with a fluid control valve 31) connects the supply line 14 (upstream of the fluid balance device 11, 12) with the discharge line 21 (downstream of the fluid balance device 11, 12).

Optionally the dialysis machine comprises a bypass block line 32 arranged internally of the cabinet 15. The bypass block line 32 exhibits two opposite ends, each of which is provided with a fluid port with a counter-connector 33 and 34 (for example a nipple with a Hansen-type connector) configured for removable connection with the connector 18 and 24 of the lines external of the cabinet 15, respectively for fresh dialysate supply 17 and for used dialysate discharge 23. Each of the two counter-connectors 33 and 34 can, for example, be of the type comprising a tubular element (nipple). The bypass block line 32 is inactive during the treatment (configuration of FIG. 1) and is active, for example, during cleaning and/or disinfecting operations on the dialysis machine (see configuration of FIG. 2). Optionally, to clean and/or disinfect the dialysate circuit, the dialysis machine comprises a cleaning and/or disinfecting device which, in the illustrated example, for reasons of simplicity is a part of the dialysate preparation device 10.

During the cleaning and/or disinfecting operations, the cleaning and/or disinfecting device places a cleaning and/or disinfecting agent (for example a chemical or thermal substance) into circulation in the circuit. The flexible tubes of the lines 17 and 23 external of the cabinet 15 are connected by the connectors 18 and 24 thereof to the counter-connectors 33 and 34 of the bypass block line 32. The various components of the above-described fluid circuit arranged internally of the cabinet 15 can thus be crossed and rinsed by the cleaning and/or disinfecting agent (FIG. 2).

Figure 2:
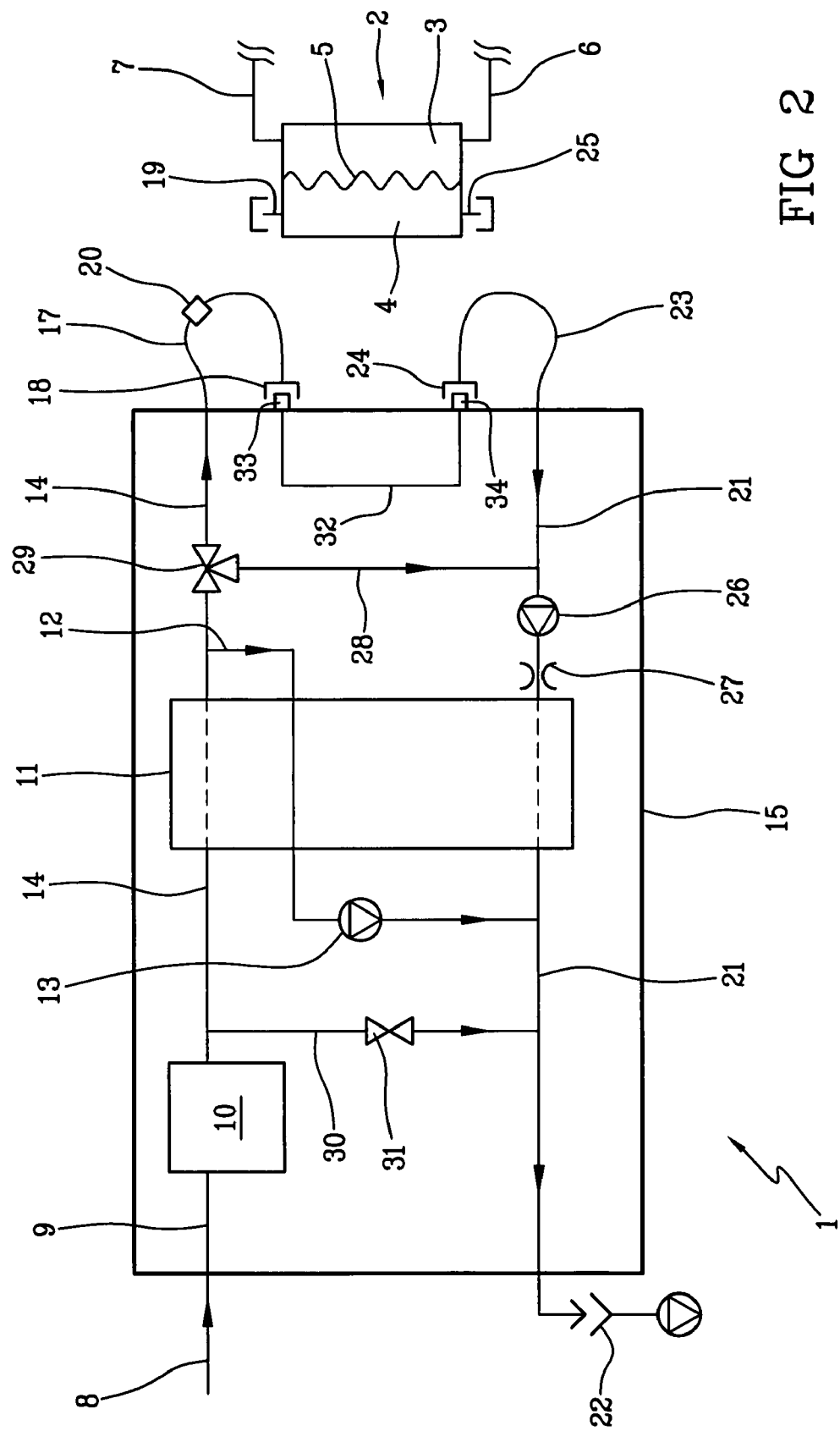
FIG. 2 illustrates the apparatus of FIG. 1 in a non-treatment configuration, for example a cleaning and/or disinfecting configuration.
Figure 3:
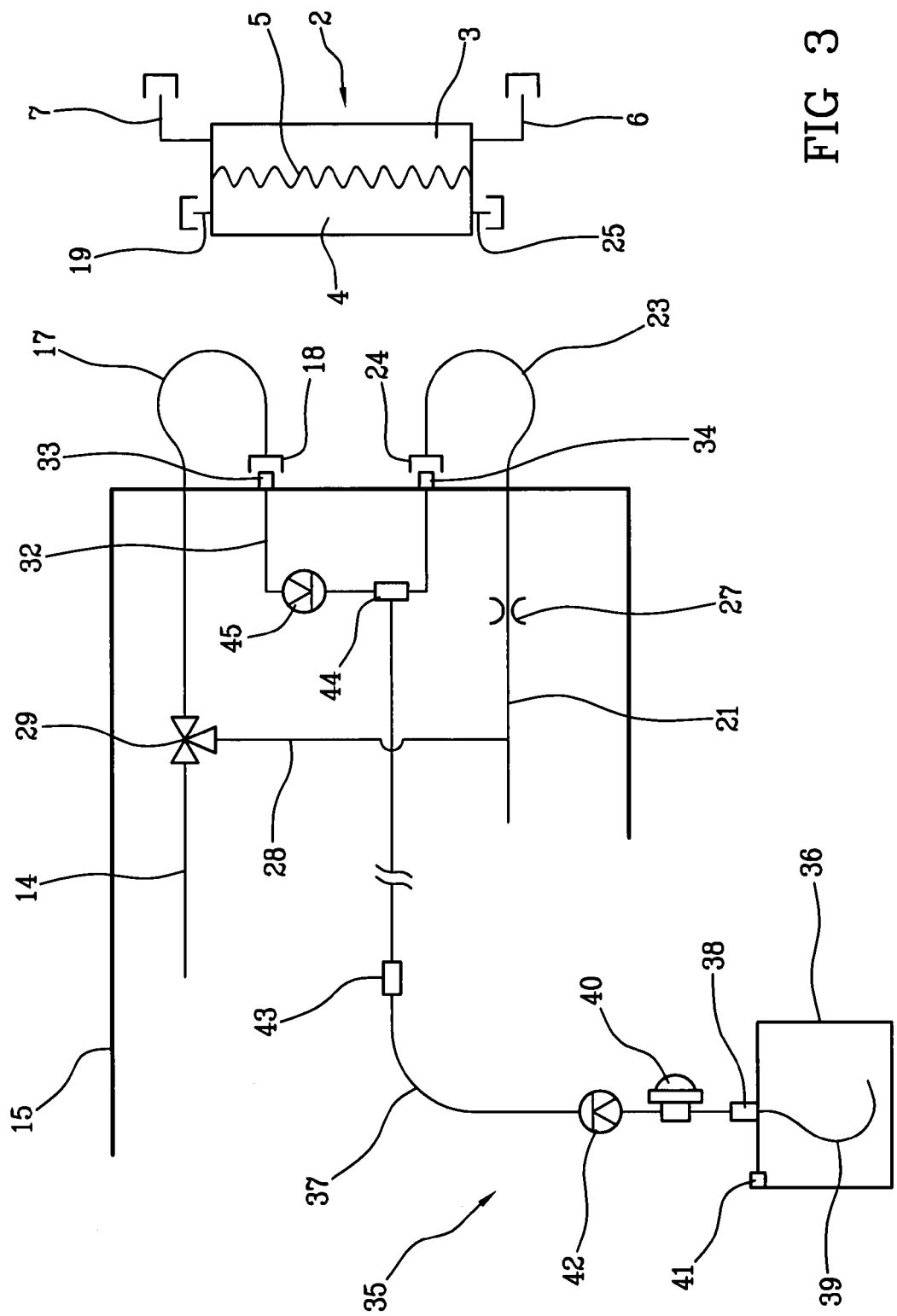
FIG. 3 illustrates a second version of an extracorporeal blood treatment apparatus, provided with a medical connector in accordance with the present invention, with the apparatus in a non-treatment configuration, for example a cleaning and/or disinfecting configuration.

The apparatus of FIG. 3 comprises all the elements of the apparatus of FIGS. 1 and 2, although some of them have not been illustrated for reasons of simplicity. The elements illustrated in FIG. 3 which are the same as elements of the apparatus of FIGS. 1 and 2 have been denoted using the same numbers. In the apparatus of FIG. 3 an automatic injection system 35 is illustrated, for introducing a cleaning and/or disinfecting agent. The automatic injection system 35 comprises a container 36 of the cleaning and/or disinfecting agent connected to a transport line 37 of the agent. Optionally, a connector 38 of known type places the container 36 and the transport line 37 in sealed fluid connection. Optionally the container 36 can be provided with an internal tube 39 which is in contact with the agent and is connected to the connector 38. The injection system 35 comprises a pump 40 (for example of the positive displacement type) for moving the cleaning and/or disinfecting agent taken from the container 36. The container 36 can be provided with an air inlet or with a vacuum release valve 41. The transport line 37 can be provided with a check valve 42 (arranged downstream of the pump 40 or incorporated thereto) for preventing a backflow of the cleaning and/or disinfecting agent towards the container 36. Optionally the transport line 37 is provided with a flow sensor 43 for detecting the existence and/or flow rate in the transport line 37. The transport line 37 of the cleaning and/or disinfecting agent is connected to the bypass block line 32, for example at a three-way junction 44 which forms an injection point of the cleaning and/or disinfecting agent into the bypass block line 32. Optionally, the bypass block line 32 can be provided with a backflow prevention valve 45 (for example a check valve) arranged between the three-way junction 44 and the counter-connector 33 destined for connection with the fresh dialysate supply line 17, 14. The valve 45 prevents backflow of the cleaning and/or disinfecting agent towards the fresh dialysate supply line 17, 14 or in any case at a point upstream of the blood treatment device 2. A possible cleaning and/or disinfecting procedure of the apparatus of FIG. 3 is described in U.S. Pat. No. 5,409,612 which is incorporated herein for reference.

Figure 4:
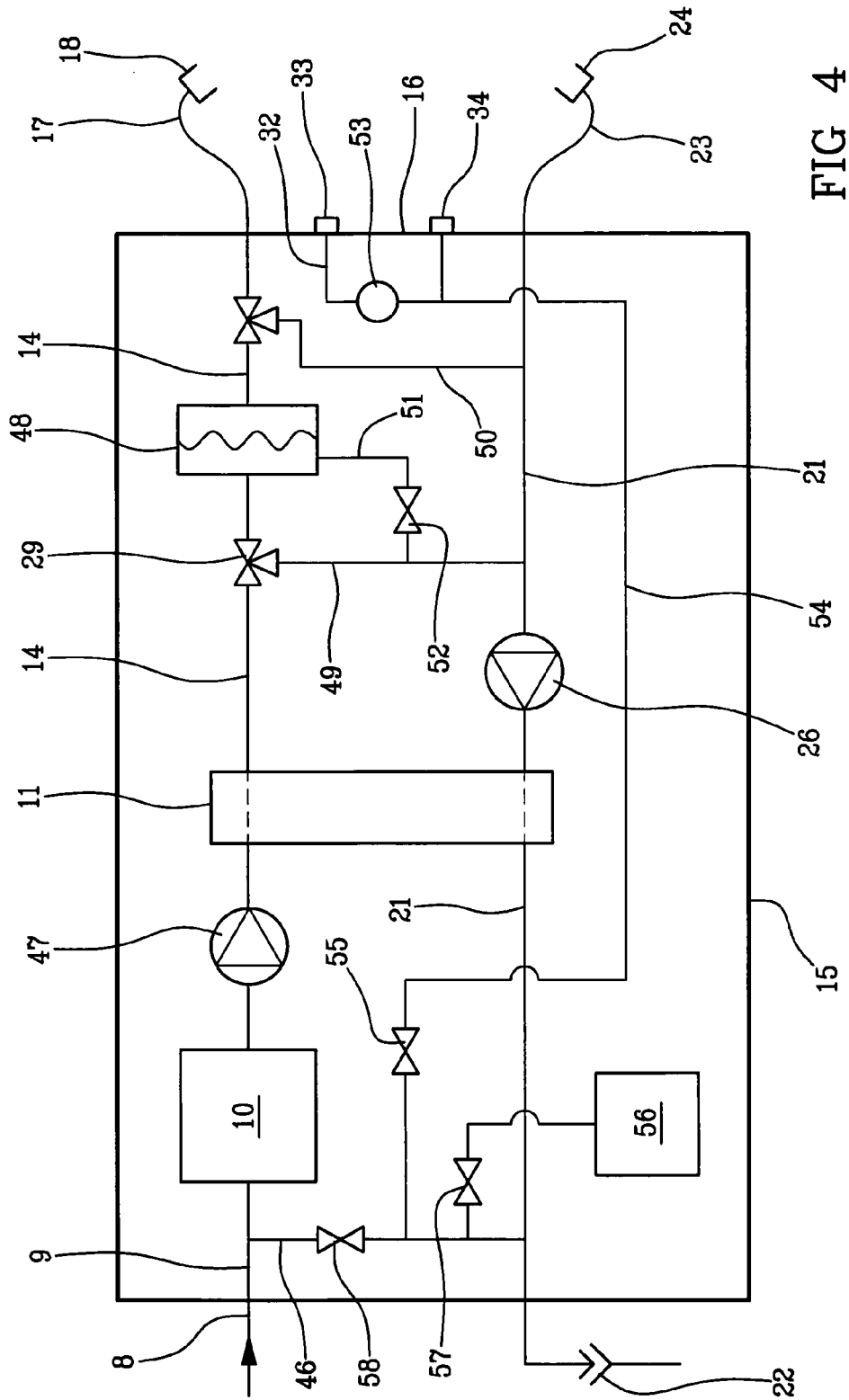
FIG. 4 illustrates a third version of an extracorporeal blood treatment apparatus, provided with a medical connector in accordance with the present invention.

The apparatus of FIG. 4 includes various elements which are in common with the apparatus of FIG. 1 and which for the sake of simplicity have been denoted using the same numbers. Optionally, the apparatus of FIG. 4 comprises a bypass line 46 (water bypass) arranged upstream of the dialysate preparation device 10 (in particular the bypass line 46 connects the fluid inlet line (water) 9 with the used dialysate discharge line 21 and is arranged before a heater, a degasser and a concentrate injector, of known type and not illustrated, which form part of the dialysate preparation device 10). Optionally, the fresh dialysate supply line 14 is provided with a circulation pump 47 of fresh dialysate which can be arranged, for example, before the fluid balance device 11 (which in the specific case is of a type having two flowmeters). Optionally the fresh dialysate supply line 14 comprises an ultrafilter 48 which performs the ultrafiltration (with a consequent purification) of the dialysate before the dialysate reaches the blood treatment device 2. Optionally two device 2 bypass lines are provided, which connect the fresh dialysate supply line 14 and the used dialysate discharge line 21, in which a first bypass line 49 is arranged between the fluid balance device 11 and the ultrafilter 48, and a second bypass line 50 is arranged between the ultrafilter 48 and the blood treatment device 2. Optionally, the ultrafilter 48 is provided with a tangential rinsing line 51 which is connected to the discharge line 21 (for example by means of the connection to a bypass line) and which is provided with a block valve 52. Optionally the bypass block line 32 is provided with a flow sensor 53 for detecting the presence of flow. Optionally the bypass block line 32 is connected to the water bypass line 46 by means of a communication line 54 provided with a fluid control valve 55 (for example a check valve controlled by the control unit of the dialysis machine). Optionally, the apparatus comprises a cleaning and/or disinfecting agent 56 (of known type, configured for supplying a cleaning and/or disinfecting agent) connected to the water bypass line 46 via a fluid control valve 57 (for example a controlled check valve for controlling the dialysis machine). The water bypass line 46 has a fluid control valve 58 arranged between the inlet line 9 and the fluid control valve 58 arranged between the inlet line 9 and the communication line 54 and the valve 57. In the cleaning and/or disinfecting procedure the connectors 18 and 24 of the dialysate lines are connected to the counter-connectors 33 and 34 of the bypass block line 32. The functioning of the cleaning and/or disinfecting device of the apparatus of FIG. 4 substantially corresponds to the cleaning and/or disinfecting procedure of a Phoenix™ produced by Gambro™, a procedure of known type (for example it is described in the technical manual accompanying the machine) and which is herein incorporated for reference.

Each of the above-described blood treatment apparatus comprises, apart from the ones already described, other various actuators for control of the extracorporeal blood treatment (for example a blood flow block valve on the venous line, a blood flow block valve on the arterial line, a dialysate heater, a dialysate degasser, etc) and various sensors for monitoring parameters connected with the extracorporeal blood treatment (for example sensors for determining the transmembrane pressure, a blood pressure presence/absence sensor on the blood circuit, an air bubble sensor on the blood circuit, pH/temperature/conductivity sensors on the dialysate circuit, etc.). The above-described actuators and sensors of the apparatus can comprise the actuators and sensors any one of the dialysis apparatus or hemo(dia)filtration apparatus of known type is provided with.

Figure 5:
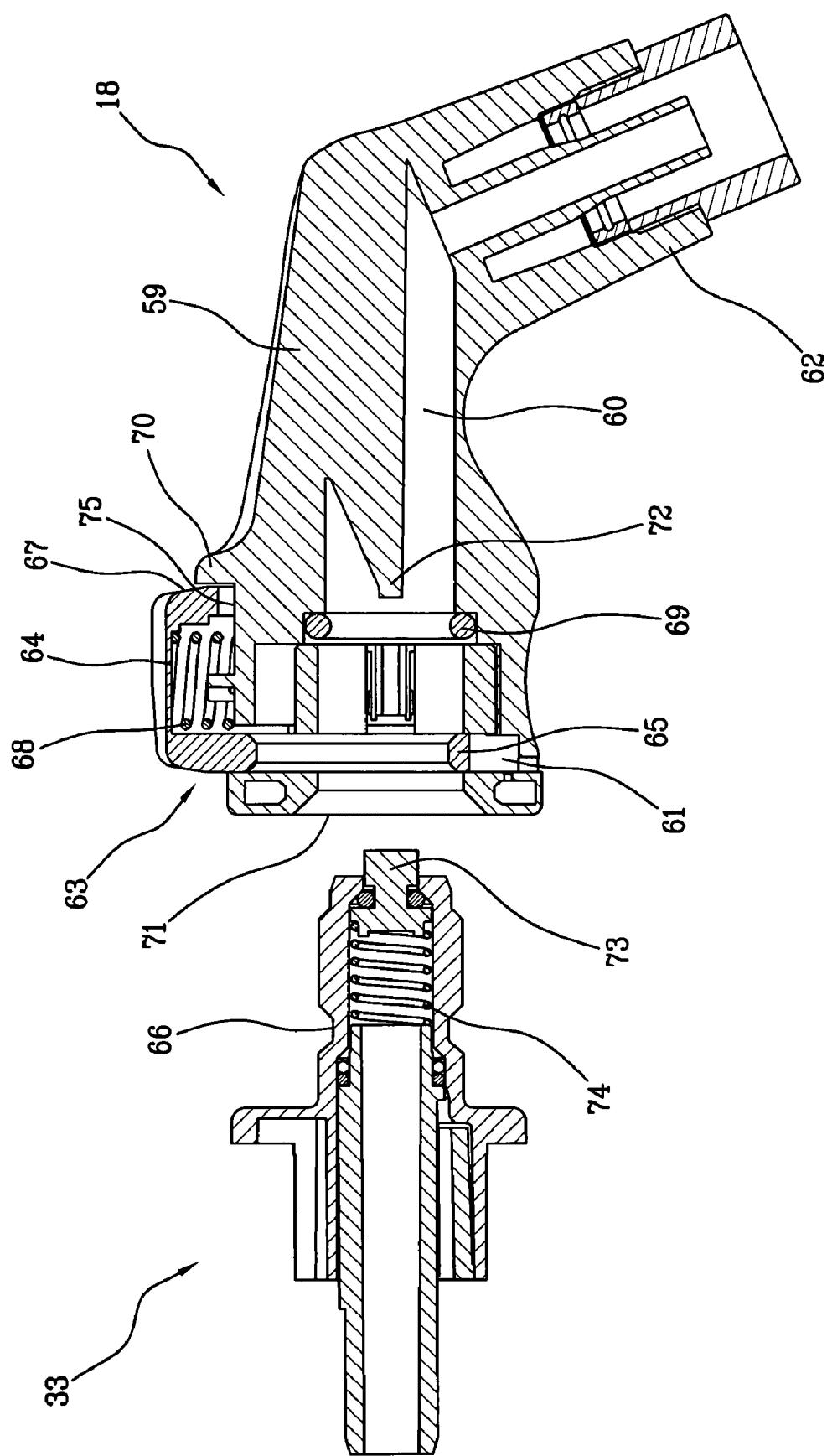
FIG. 5 illustrates in greater detail a second of the nipple 33 (or 34) and the medical connector 18 (or 24) indicated only schematically in figures from 1 to 4, with the nipple and the medical connector distanced from one another.
Figure 6:
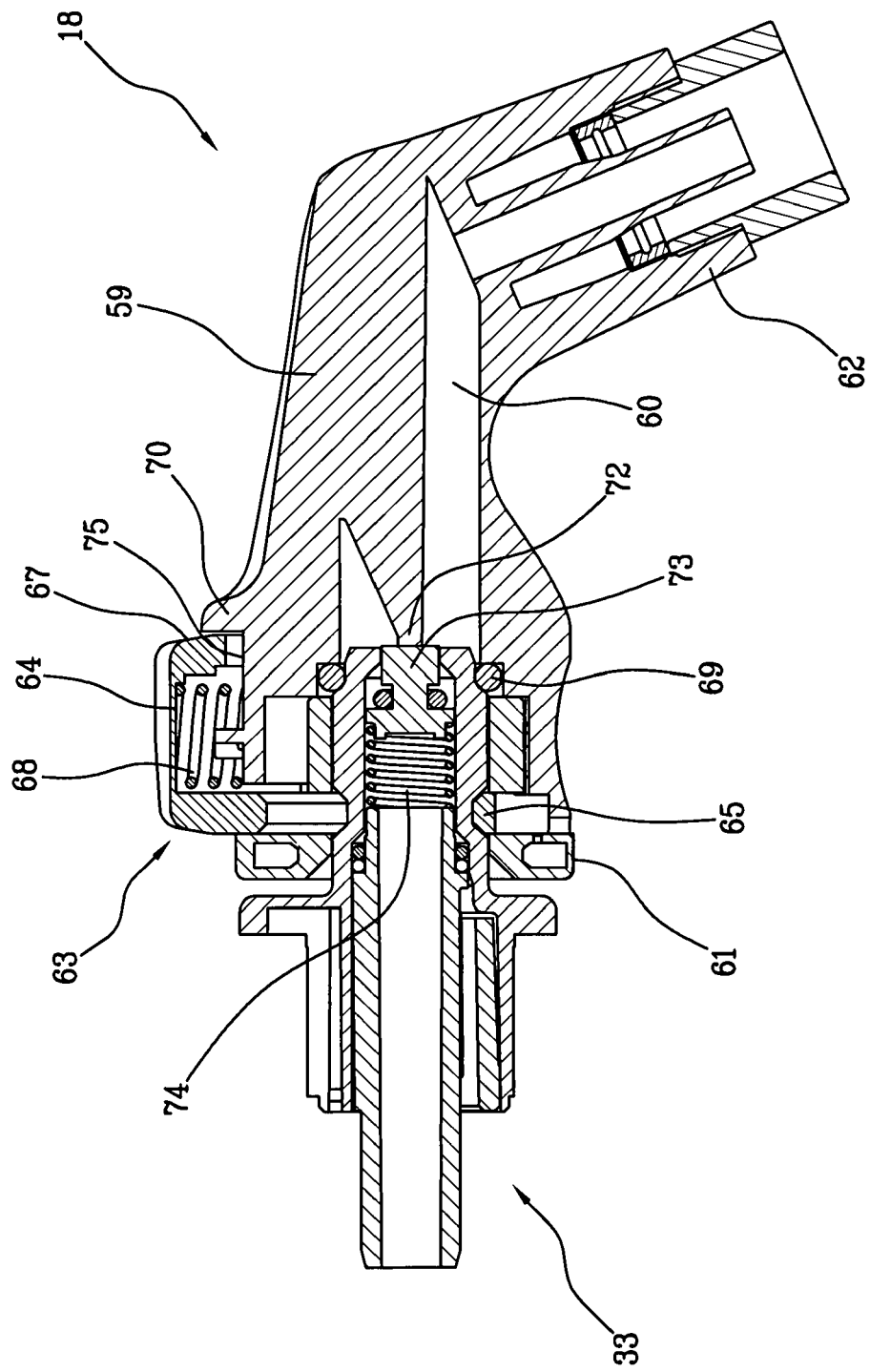
FIG. 6 illustrates the nipple and the connector of FIG. 5 in a correctly coupled configuration.
Figure 7:
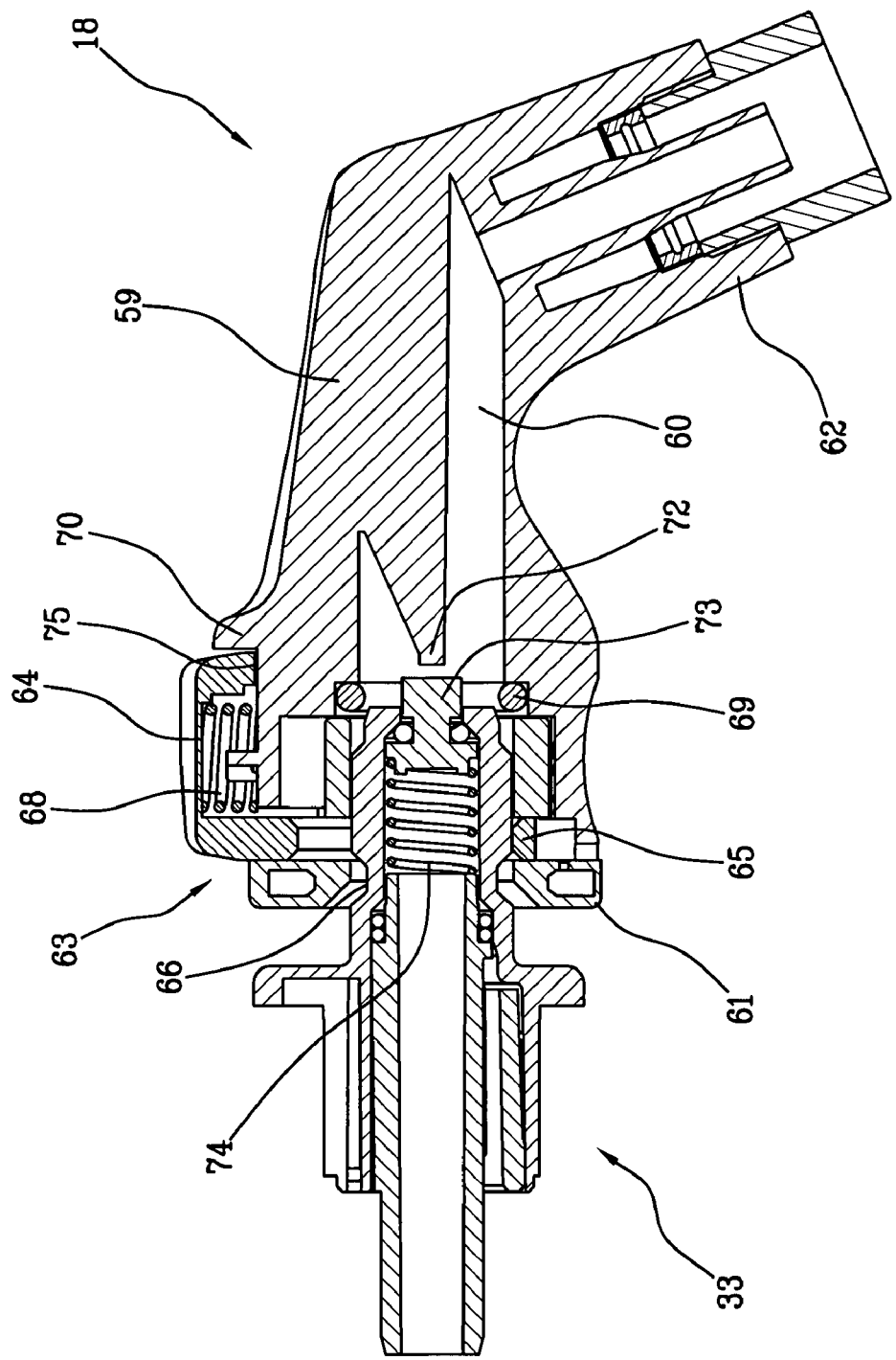
FIG. 7 illustrates the nipple and the connector of FIG. 5 in a transitory insertion configuration or an incorrect coupling configuration.
Figure 8:
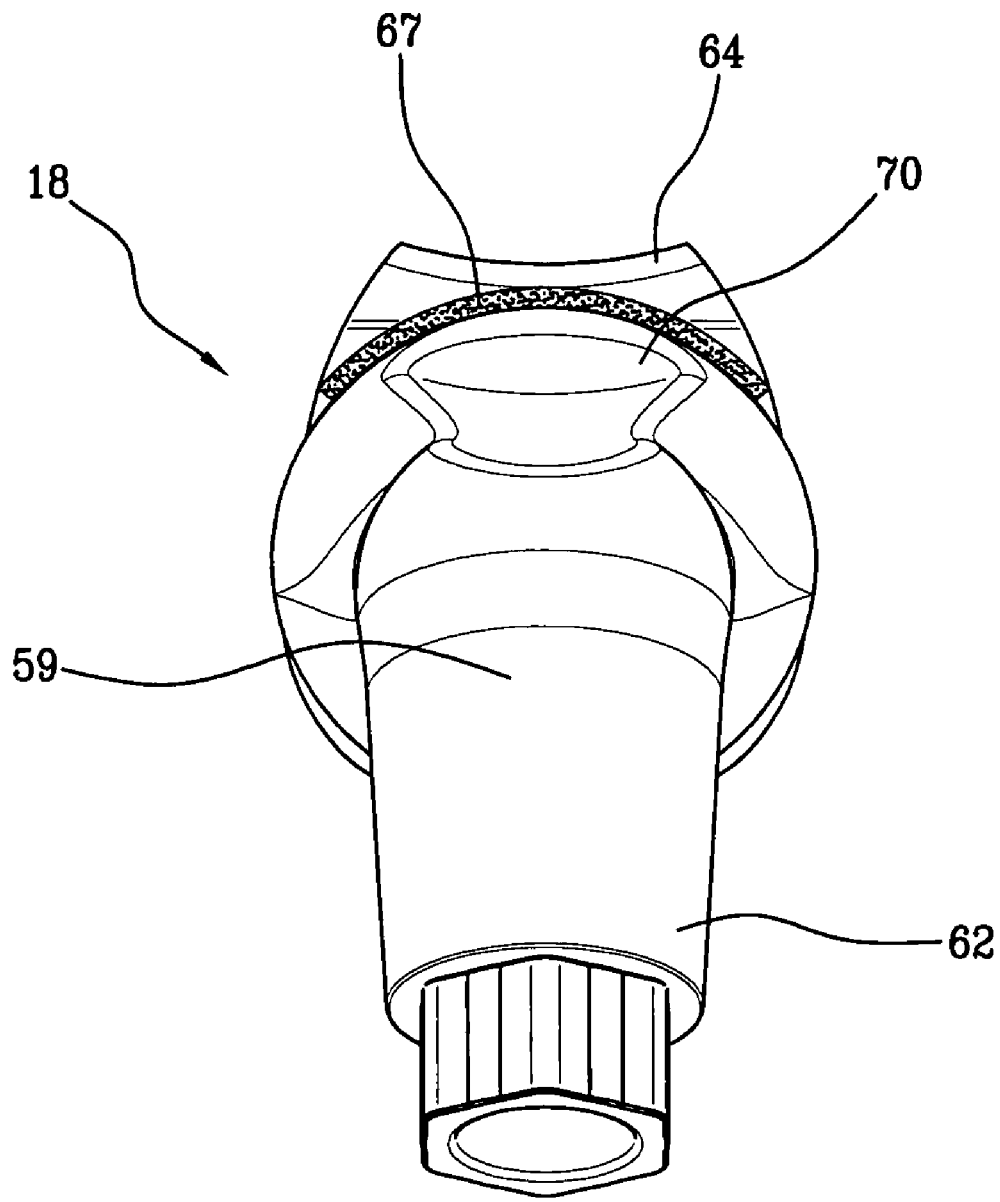
FIG. 8 is a front view with the nipple and the connector in the correct coupling configuration.
Figure 9:
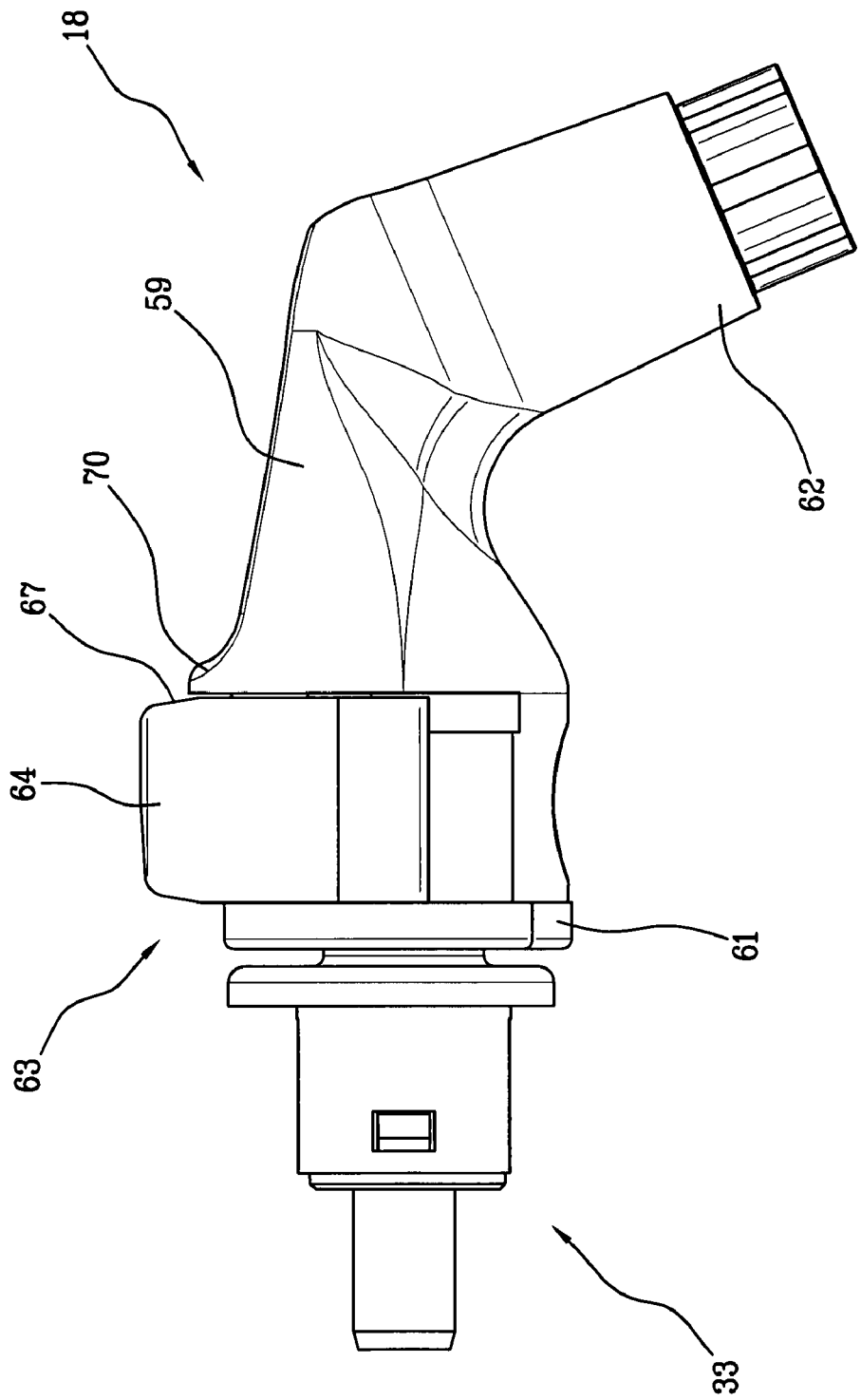
FIG. 9 is a lateral view with the nipple and the connector in the correct coupling configuration.
Figure 10:
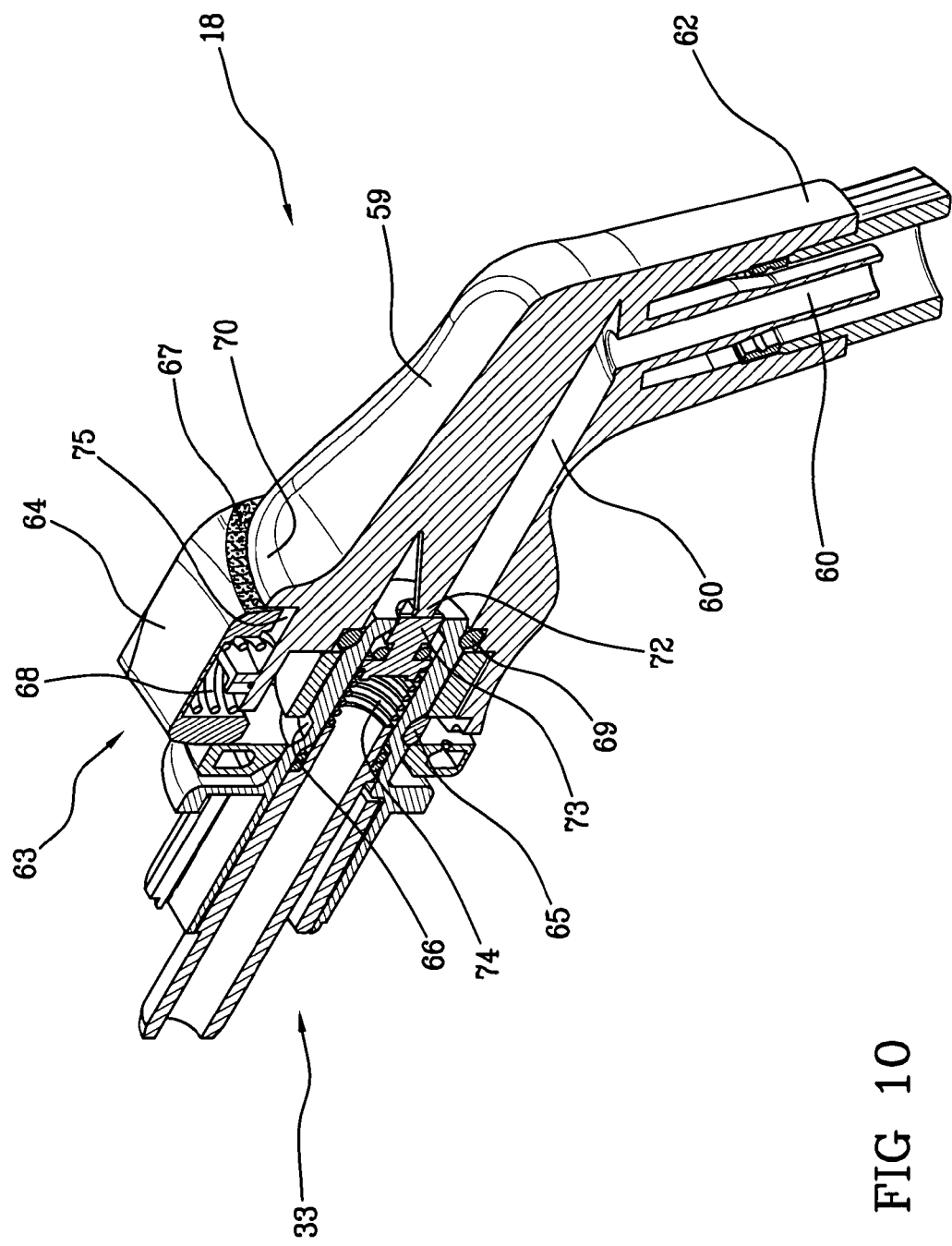
FIG. 10 is a sectioned perspective view with the nipple and the connector in the correct coupling configuration.
Figure 11:
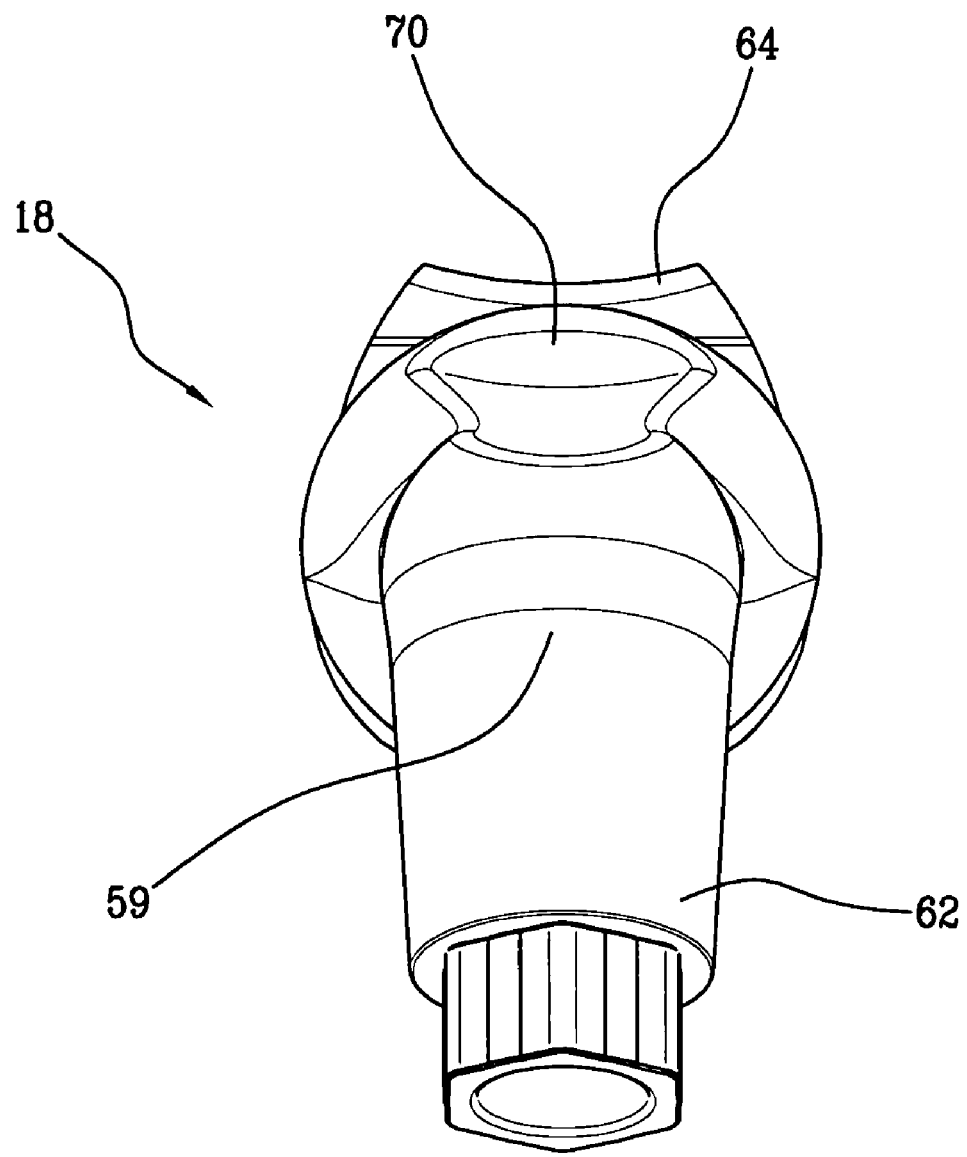
FIG. 11 is a front view with the nipple and the connector in a transitory insertion configuration or an incorrect coupling configuration.
Figure 12:
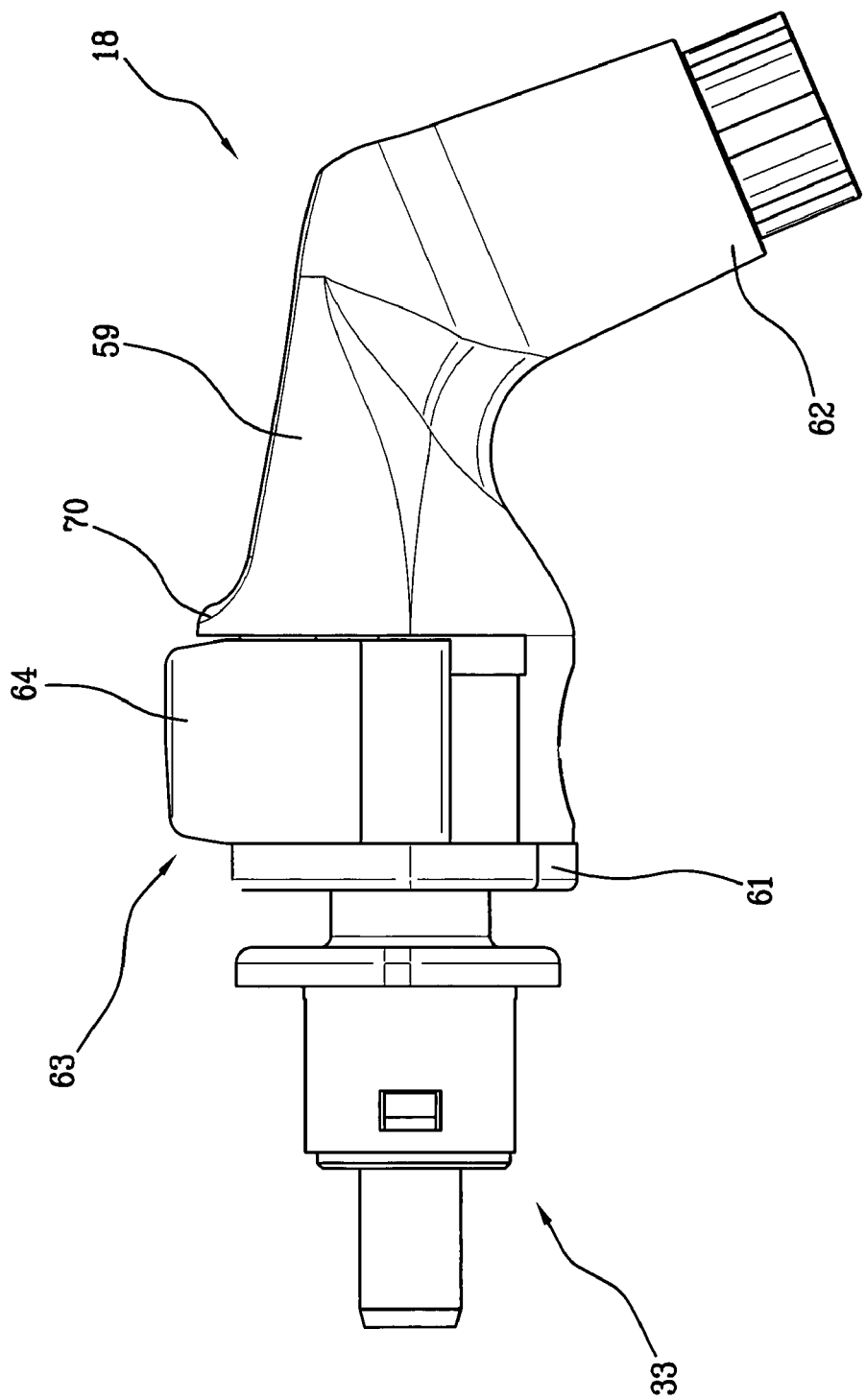
FIG. 12 is a lateral view with the nipple and the connector in a transitory insertion configuration or an incorrect coupling configuration.
Figure 13:
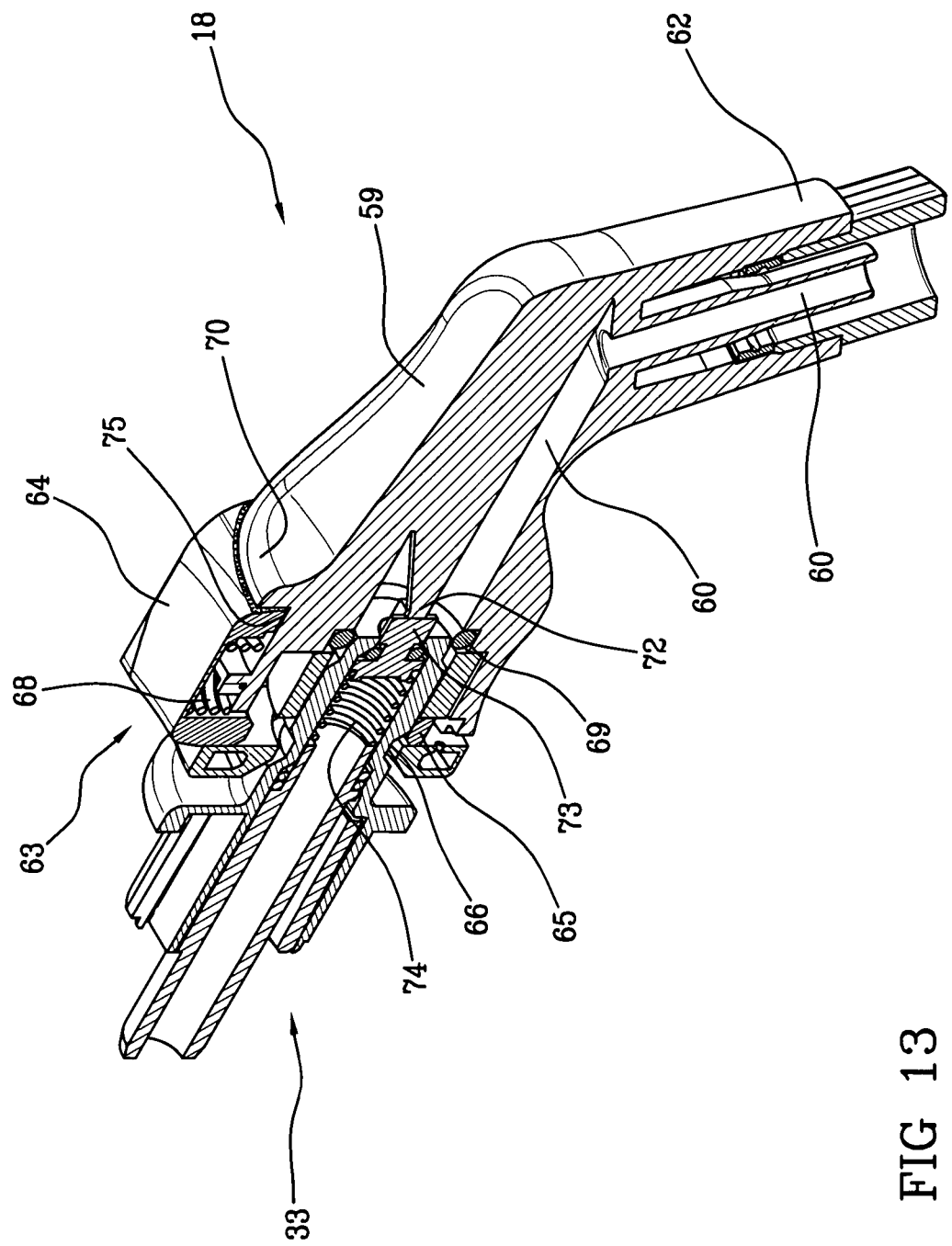
FIG. 13 is a sectioned perspective view with the nipple and the connector in a transitory insertion configuration or an incorrect coupling configuration.

In figures from 5 to 17 the medical connector 18 or 24 (which are substantially identical) is described in detail, which is arranged at the end of each of the flexible parts 17 and 23 of the fresh dialysate line and the used dialysate line. The medical connector 18, to which reference will be made hereinafter for simplicity (keeping in mind that the other connector 24 is substantially identical), comprises a connector body 59 crossed by a cavity 60. The connector body 59 can be realised in a single piece or in several pieces which are assembled to one another (assembled removably or permanently). The connector body 59 has a first end 61 which surrounds the cavity 60 and a second end 62, opposite the first end, which surrounds the cavity 60. Optionally the first end 61, as also optionally the second end 62, can be of any tubular shape. The two ends 61 and 62 can be coaxial or, as in the specific case, can define two non-coincidental axes. These non-coincidental axes can be parallel or, as in the specific case, not parallel but forming an angle which, in the specific case, is greater than a right angle. The first end 61 is configured for coupling (normally removable) with an access port (inlet or outlet) to the fluid chamber 4 of the extracorporeal blood treatment device of the semipermeable membrane type. The second end 62 is configured for coupling (stable or removable) with the flexible tube (manoeuvrable) located at the end of the supply line 17 or the discharge line 23 of the dialysate circuit. In the specific case a second end 62 is illustrated, which is provided with a connecting system to the flexible tube of a certain type, but it is however possible to use a second end 62 provided with any known type of tube connecting system. The first end 61 defines an insertion axis into the cavity of an external tubular element. The external tubular element can comprise the access port of a dialyser, or the nipple (illustrated in FIG. 5) or counter-connector 33 or 34 (the counter connectors 33 and 34 being substantially the same as each other) arranged at an end of the bypass block line 32 on the front panel 16 of the dialysis machine. Optionally the connector body 59 is realised in plastic.

Figure 14:
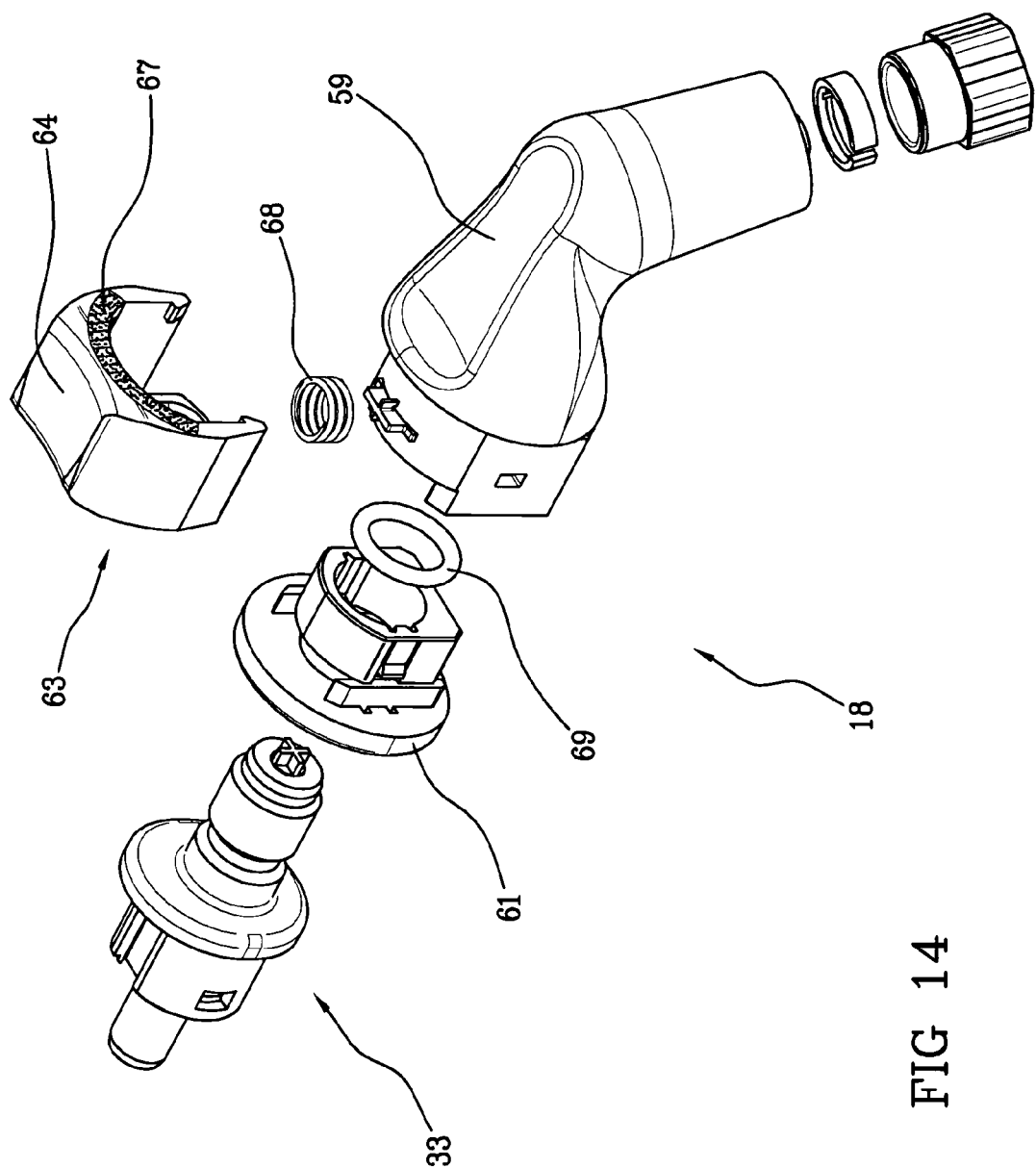
FIG. 14 is an exploded view of the nipple and the connector of FIG. 5.

The first end 61 of the connector body 59 has a lateral surface exhibiting a recess 75. The medical connector 18 comprises an engaging element or latch 63 having a manoeuvring portion 64 which is at least partially lodged in the recess 75 and a manoeuvring portion 65 which is at least partially lodged in the cavity 60. The latch 63 is mobile and can assume at least an engagement position (FIGS. 6, 8, 9, 10) and at least an insertion position (FIGS. 7, 11, 12, 13). In the engagement position the manoeuvring portion 64 emerges from the recess 75 and the engagement portion 65 narrows a second of the cavity 60 in order to engage with an undercut of the external tubular element (for example the counter-connector 33) inserted in the cavity 60. In the specific case illustrated in the figures, the undercut is formed by an annular gulley 66 afforded on the external lateral surface of the main body of the counter-connector or nipple 33. In the insertion position the manoeuvring portion 64 enters the recess 75 and the engagement portion 65 does not narrow the above-mentioned section of the cavity 60 in order to all insertion of the external tubular element 33 in the cavity. The first end 61 of the connector body 59 and the latch 63 are configured so as to couple with an external tubular element comprising a fluid passage port (for example the port 19 or the port 25) borne by a semipermeable membrane device for extracorporeal blood treatment. Optionally the latch 63 is slidable on axial guides borne by the connector body 59 (the guides are visible in the exploded view of FIG. 14, where it can also been seen that in the specific case the connector body 59 is made of several parts assembled together). The axial guides are, in the example, perpendicular to the insertion axes in the cavity defined by the first end 61.

The connector body 59 has, overall, a curved longitudinal development in order to be easily gripped. In particular a central part of the connector body 59 is easily grippable, while the manoeuvring portion 64 of the lock 63 arranged on the first end 61 is easily reachable with a finger (for example the thumb) of the operator in order to be pressed such that it is like an engagement button of the connector.

The manoeuvring portion 64 has an external surface which exhibits a signal 67. The signal 67 is conformed and arranged such as to exit from the recess 75 in the engagement position in order to be visible by an external observer. In particular the signal 67 is arranged such as to be easily visible by the operator holding the connector body 59. The signal 67 is further conformed and arranged such as to enter the recess 75 in the insertion position in order to be hidden from the operator's view. In particular the signal 67 is hidden inside the recess 75 when the operator keeps the manoeuvring portion 64 pressed downwards, or when the manoeuvring portion 64 itself, for any reason, is not in or does not return to the raised position in which it emerges from the recess 75. Optionally the visible signal 67 comprises a patch which is coloured differently to the colour of the surface of the manoeuvring portion 64 arranged about the signal itself. The coloured patch can be realised, for example, by means of simple silk screening. The signal 67 is coloured such as to be distinctly seen by an operator, for example in green or red. Optionally the signal 67 lies on a perpendicular plane to the insertion axis in the cavity 60 across the first end 61. Optionally the signal 67 lies on a plane which is parallel to a movement direction of the latch 63 between the above-cited engagement and insertion positions.

Optionally the medical connector 18 (or 24) comprises elastic means configured to exert a force which brings the latch 63 towards the engagement position. In the specific case the elastic means comprise an elastic body 68 (for example a spring) arranged in a hollow seating afforded in the first end 61. The manoeuvring portion 64 has a dome shape internally of which the elastic body 68 is housed. The elastic means can operate contactingly with the latch 63 on one side and with the first end 61 of the connector body 59 on the other side. Optionally the medical connector 18 (or 24) comprises means for sealing predisposed to create a fluid seal on the counter-connector (nipple 33) inserted in the cavity 60. The means for sealing can comprise, for example, a seal ring 69 (in the specific case a removable-type seal housed in the cavity 60 and borne by the first end 61).

Optionally the first end 61 of the connector body 59 has a recess wall 70 which delimits the recess 75 and which directly faces the signal 67 in the insertion position. The recess wall 70 is parallel to the direction of movement of the latch 63 between the engagement position and the insertion position. Optionally the recess wall 70 has a first curved external profile; the visible signal 67 has a second curved external profile having a shape which can substantially be superposed on the first curved external profile of the recess wall 70 the visible signal 67 is, optionally, strip-shaped and extended in length parallel to the edge of the recess wall 70. The strip can be, for example, a circular crown sector shape.

The manoeuvring portion 64 has a first side facing towards the same direction (on the left in FIG. 5) in which the insertion opening 71 faces the insertion opening 71 being defined by the first end 61 of the connector body 59. The insertion opening 71 is the opening through which the external tubular element (nipple or counter-connector 33) is inserted in the cavity 60. Optionally the signal 67 is arranged on a second side of the manoeuvring portion 64 opposite the first side. Substantially the signal 67 faces in an opposite direction with respect to the insertion opening 71.

Figure 15:
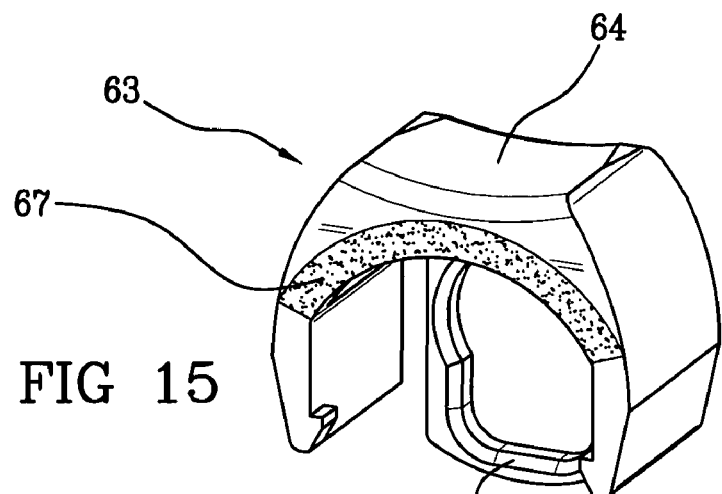
FIG. 15 is a perspective view of a component (engaging element or latch 63) of the medical connector bearing the visual signal 67.
Figure 16:
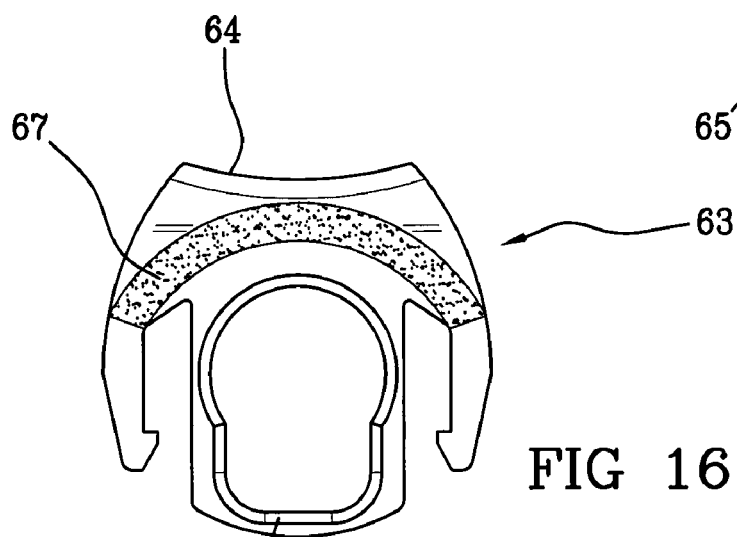
FIG. 16 is a frontal view of the component of FIG. 15.
Figure 17:
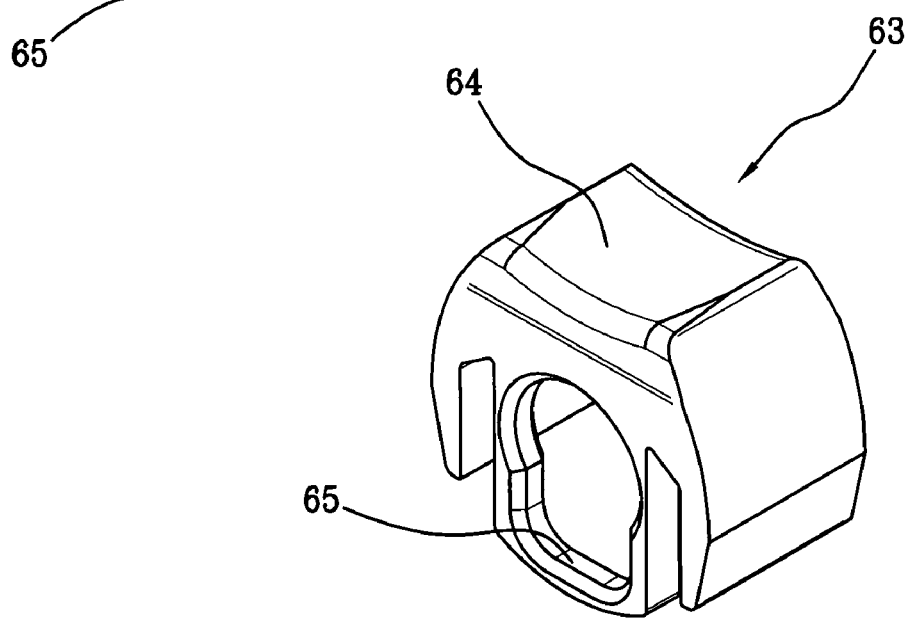
FIG. 17 shows the component of FIG. 15 in a further perspective view.

In FIGS. 15 to 17, in which the latch 63 is illustrated, it can be seen that the engagement portion 65 optionally has an arched shape and is optionally realised in a single piece with the manoeuvring portion 64 which exhibits the surface bearing the visible signal 67.

Optionally the medical connector 18 (or 24) comprises a pusher element 72 arranged internally of the cavity 60. The pusher element 72 projects in an axial direction, i.e. in a substantially parallel direction to the insertion axis in the cavity 60 of the external tubular element. The engagement portion 65 is arranged between the insertion opening 71 and the pusher element 72. The pusher element 72 is configured such as to interact contactingly with the external tubular element inserted in the cavity 60, so that, in the correct insertion configuration of the external tubular element, the pusher element 72 displaces a cap 73 into open position, which cap 73 normally closes the fluid inlet of the tubular element. The opening of the cap 73 leads to the sealed fluid connection between the external tubular element and the medical connector. In the specific case, the cap 73 is normally kept closed by an elastic element 74. The pusher element 72 thus operates antagonistically with the elastic element 74. The opening action of the pusher element 72 is fully effective only in the correct connection position, i.e. in the position in which the manoeuvring portion 64 is in the engagement position, in which it is coupled with the undercut defined by the gulley 66. If, on the act of coupling between the medical connector and the external tubular element, the latch 63 (comprising the manoeuvring portion 64 and the engagement position 65) remains in the insertion position or, in any case, it does not return into the engagement position, it can happen that the cap 73 of the nipple 33 or 34 stays closed or is not completely opened by the pusher element 72, so that the connection is not correct.

The manoeuvring portion 64 is in the engagement position (the raised position in which it emerges from the recess 75 enabling the signal 67 to be seen) both when the medical connector 18 (or 24) is coupled correctly with an external tubular element (nipple or counter-connector 33 or 34, or access port 19 or 25 to the fluid chamber 4), and when the medical connector 18 is free and totally disengaged from the external tubular element. The manoeuvring portion 64 is in the insertion position (lowered position in which it is in the recess 75 so as to hide the signal 67 from view) both in the transitory coupling stage in which the medical connector 18 (or 24) is coupled with the external tubular element, and in the undesirable circumstance in which the medical connector has been coupled incorrectly, partially or imprecisely, with the external tubular element. Once the operator has performed the coupling between the medical connector 18 (or 24) and the external tubular element (for example the nipple 33 or 34 on the front panel 16 of the machine or the fluid port 19 or 25 on the dialyser body), the operator can verify securely and immediately whether the connection has been made correctly or not, simply by checking whether the signal 67 arranged on the manoeuvring portion 64 is visible or not. If, once the coupling has been made, the button formed by the manoeuvring portion 64 is not raised, the signal 67 remains hidden by the wall 70 and is therefore not visible, giving the visible signal of incorrect position and coupling. In this faulty configuration it can occur that, for example, the pusher element 72 is not able to open the cap 73 or to open it only partially. If, in this situation, the operator gives the command to perform the washing and/or disinfection procedures, considerable drawbacks for the dialysis apparatus might ensue, such as for example overpressures in the fluid circuit, with damage to the tubes, the sensors and other elements making up the circuit, such as fluid loss, tube detachment, etc.

As mentioned above, an incorrect opening of the nipple 33 or 34 can lead to various drawbacks, particularly (though not only) during the stage of washing and/or disinfecting the machine, such a loss of fluid or overpressures with a risk of damaging the fluid circuit internal of the cabinet. The incorrect coupling of the medical connector 18 (or 24) with the fluid port 19 (or 25) of the blood treatment device 2 can lead to several drawbacks, both during the treatment stage and during the procedures which are normally performed before and after the treatment itself, which drawbacks might be, for example, the loss of dialysate or insufficient supply of the dialysate or detachment of the tubes.

The fact that the medical connector is provided with a visual signalling means of the correct engagement position of the connector provides a simple and practical system for the operator immediately to become aware of a faulty situation and thus be in a position to take the necessary steps (for example resetting a correct connection) before proceeding with the successive operations, such as for example the cleaning and/or disinfection of the extracorporeal blood treatment or the preliminary procedures to the extracorporeal treatment.

The above-mentioned visual signalling means can also be applied to other types of medical connectors in which on connecting-up an engagement element is displaced radially or transversally (in general neither circumferential nor axial) with respect to the insertion axis of the connector in the counter-connector (in general this axis can coincide with the movement direction of a fluid which in use flows through the coupled connector and the counter-connector). The above-mentioned visual signalling means is arranged on the mobile engaging element such as to be able to assume a first position in which it is visible to the operator and a second position in which it is hidden from the operator, as it is located behind a wall, or abutment, or projection, borne by the connector or the counter-connector. The first position can be, for example, the correct engagement position, while the second position can be a faulty engagement position.

The above-mentioned visual signalling means can be applied, for example, to the connector arranged at the end of the acid/acetate line borne by the dialysis machine going by the name of Phoenix™ produced by Gambro™. This connector, of known type and not illustrated, being of the above-cited type, can be provided with a coloured screen-applied patch or another visual signalling means which is visible in a first position of the mobile engaging element and is hidden in a second position. In use the connector of the acid/acetate line is connected to a batch container of acid concentrate (for bicarbonate dialysis) or acetate concentrate (for acetate dialysis). When not in use (for example during rinsing and at rest) the connector is connected to a rinsing port arranged on the machine panel. This rinsing port can be provided, as in the Phoenix™ dialysis machine, with a counter-connector in the form of a nipple. If the connector is not correctly connected to the counter-connector (for example it is not connected fully, up to end-run of axial insertion), the visual signalling means is hidden, or it is visible according to the convention adopted for recognising the faulty situation; if, for example, the visual signalling means comprises a green-coloured band, the alarm signalling system can have the band hidden or invisible in incorrect engagement position, and not hidden or visible in the opposite case: if, on the other hand, the visual signalling means comprises a red-coloured band, the alarm signalling system might have the band not hidden or visible in a case of incorrect engagement position and hidden or visible in the opposite case. The visual signalling means can be located or associated or borne by the mobile element of the connector, in particular on a surface of the mobile element which is hidden behind a fixed element of the connector when the mobile element is pressed in order to enable coupling with the counter-connector.

The above-described visual signalling means can be applied, in other examples, to the connector arranged at the end of the bicarbonate line borne by the Phoenix™ dialysis machine realised by Gambro™ and/or to the connector arranged at the end of the disinfecting line of the Phoenix™ machine. Each of the above connectors is the same from the structural point of view and the mechanical functioning point of view as the above-mentioned connector of the acid/acetate line. The bicarbonate line is configured for connection, in use, with a bicarbonate concentrate container. When not in use (for example because a different source of bicarbonate concentrate is in use, or during an acetate dialysis, or during rinsing, or when the machine is at rest) the connector of the bicarbonate line is coupled to a respective rinsing port on the machine panel (alike to the rinsing port of the acid/acetate line and thus also provided with a counter-connector, for example a nipple). The disinfecting line is configured for connection with a chemical disinfectant container. When not in use (for example during the main operative stages of the machine) the connector of the disinfectant line is coupled to a rinsing port on the machine panel (alike to the rinsing port of the acid/acetate line).

Numerous modifications of a practical/applicative nature can be brought to the constructional details of the invention, without its forsaking the ambit of protection sought for the inventive idea, as claimed herein below.

The invention claimed is:

1. A medical connector, comprising:
a connector body crossed by a cavity, the connector body having a first end which surrounds the cavity and a second end which surrounds the cavity; the first end defining an insertion axis of an external tubular element into the cavity; the connector body having a lateral surface exhibiting a recess;
an engaging element having a manoeuvring portion at least partially housed in the recess and an engaging portion configured for coupling with the external tubular element; the engaging element being mobile with a possibility of assuming at least an engaged position, in which it is coupled with the external tubular element, and at least an inserted position, in which the external tubular element can insert into the cavity; the manoeuvring portion emerging from the recess in the engaged position and returning into the recess in the inserted position; and
at least a signal associated to an external surface of the manoeuvring portion, the signal being conformed and arranged such as to exit from the recess in the engaged position in order to be visible to an external observer, and such as to return into the recess in the inserted position in order to be hidden from view, wherein the signal is a visual signal and comprises a coloured patch applied to the external surface of the manoeuvring portion.

2. The connector of claim 1, wherein the engaging element is mobile between the engaged position and the inserted position in a movement direction having at least a radial motion component with respect to the insertion axis.

3. The connector of claim 2, wherein the movement direction is radial with respect to the insertion axis.

4. The connector of claim 1, wherein the engaging portion is at least partly housed in the cavity.

5. The connector of claim 1, wherein, in the engaged position, the engaging portion narrows a section of the cavity in order to engage with an undercut of the tubular external element inserted in the cavity.

6. The connector of claim 1, wherein, in the inserted position, the engagement portion does not narrow the section of the cavity in order to enable insertion of the external tubular element into the cavity.

7. The connector of claim 1, wherein the coloured strip is in a strip shape.

8. The connector of claim 1, wherein the visual signal lies on a plane which is perpendicular to the insertion axis.

9. The connector of claim 1, wherein the visual signal lies on a plane which is parallel to a movement direction of the engaging element between the engaged position and the inserted position.

10. The connector of claim 1, comprising elastic means configured for exerting a force which brings the engaging element towards the engaged position.

11. The connector of claim 1, wherein the first end has a recess wall which delimits the recess and which directly faces the signal in the inserted position.

12. The connector of claim 11, wherein the recess wall is parallel to a movement direction of the engaging element between the engaged position and the inserted position.

13. The connector of claim 11, wherein the recess wall has a first curved external profile, the signal having a second curved external profile having a shape which is substantially superposable on the first curved external profile.

14. The connector of claim 1, wherein the maneuvering portion has a first side facing in a same direction towards which direction an insertion opening faces, which insertion opening is defined by the first end, through which insertion opening the external tubular element is inserted into the cavity, the visual signal being arranged on a second side of the manoeuvring portion opposite the first side.

15. The connector of claim 1, wherein the first end and the engaging element are configured to couple with an external tubular element comprising a fluid passage port borne by a semipermeable membrane device for extracorporeal blood treatment.

16. The connector of claim 1, comprising a pusher element arranged internally of the cavity and projecting in a parallel direction to the insertion axis.

17. The connector of claim 1, wherein the recess is located on a lateral surface of the first end.

18. An extracorporeal blood treatment apparatus, comprising:
a membrane device for extracorporeal blood treatment comprising a first chamber and a second chamber which are separated from one another by a semipermeable membrane, the first chamber and the second chamber each being provided with at least a fluid passage port;
at least a fluid transport line having a first end provided with a medical connector configured for removably coupling with the fluid passage port;
wherein the medical connector is according to claim 1.

19. The apparatus of claim 18, comprising:
a drainage for a used fluid;
a nipple configured for removably coupling with the medical connector;
a fluid circuit connecting the drainage with the nipple, the fluid circuit having one or more actuators for control of the extracorporeal blood treatment and one or more sensors for monitoring parameters connected to the extracorporeal blood treatment.

20. A dialysis machine, comprising:
a source of a fresh dialysis fluid;
a drainage for a used dialysis fluid;
a fresh dialysis fluid supply line having a first end connected to the source and a second end provided with a first connector according to claim 1;
a used dialysis fluid discharge line having a first end connected to the drainage and a second end provided with a second connector, according to claim 1;
a bypass line having a first end and a second end, respectively provided with a first nipple and a second nipple, which are configured for removably coupling respectively with the first connector and the second connector.

21. The machine of claim 20, comprising a cabinet which at least partly contains the supply line, the discharge line and the bypass line; the cabinet having at least an external panel from which the first nipple and the second nipple emerge; the second end of the supply line being borne by a first tract of flexible line which emerges from the external panel; the second end of the discharge line being borne by a second tract of flexible line which emerges from the external panel.

* * * * *

UNITED STATES PATENT AND TRADEMARK OFFICE
CERTIFICATE OF CORRECTION

PATENT NO. : 8,366,648 B2  
APPLICATION NO. : 12/742629  
DATED : February 5, 2013  
INVENTOR(S) : Salvatore Sanna Page 1 of 1

It is certified that error appears in the above-identified patent and that said Letters Patent is hereby corrected as shown below:

In the Claims:

At column 12, line 51, claim 33, after "coloured", please delete "strip" and insert therefor --patch--.

Signed and Sealed this  
Seventh Day of May, 2013

Teresa Stanek Rea  
*Acting Director of the United States Patent and Trademark Office*

UNITED STATES PATENT AND TRADEMARK OFFICE
CERTIFICATE OF CORRECTION

PATENT NO.       : 8,366,648 B2
APPLICATION NO.  : 12/742629
DATED            : February 5, 2013
INVENTOR(S)      : Salvatore Sanna Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 498 days.

Signed and Sealed this

First Day of September, 2015

Michelle K. Lee
*Director of the United States Patent and Trademark Office*